(12) United States Patent
Hsieh

(10) Patent No.: US 8,858,230 B2
(45) Date of Patent: Oct. 14, 2014

(54) ARTIFICIAL ROOT FOR DENTAL IMPLANTATION AND METHOD FOR MANUFACTURING THE SAME

(75) Inventor: Pei-Hsung Hsieh, Tuchng (TW)

(73) Assignee: Biodenta Swiss AG, Berneck (CH)

( * ) Notice: Subject to any disclaimer, the term of this patent is extended or adjusted under 35 U.S.C. 154(b) by 979 days.

(21) Appl. No.: 12/250,362

(22) Filed: Oct. 13, 2008

(65) Prior Publication Data

US 2010/0092920 A1   Apr. 15, 2010

(51) Int. Cl.
*A61C 8/00* (2006.01)

(52) U.S. Cl.
CPC ............. *A61C 8/0022* (2013.01); *A61C 8/0025* (2013.01)
USPC ....................................................... 433/174

(58) Field of Classification Search
USPC .......... 433/172–176, 225; 411/411, 412, 426; 606/275, 315, 316, 317
See application file for complete search history.

(56) References Cited

U.S. PATENT DOCUMENTS

| | | | | |
|---|---|---|---|---|
| 23,409 A | * | 3/1859 | Thom | 411/411 |
| 1,827,615 A | * | 10/1931 | Rosenberg | 411/386 |
| 3,233,500 A | * | 2/1966 | Devellier | 411/413 |
| 5,964,768 A | * | 10/1999 | Huebner | 606/317 |
| 6,220,860 B1 | * | 4/2001 | Hansson | 433/173 |
| 6,454,506 B1 | * | 9/2002 | Keller et al. | 411/387.4 |
| 6,743,233 B1 | * | 6/2004 | Baldwin et al. | 606/323 |
| 6,896,517 B1 | | 5/2005 | Bjorn et al. | |

FOREIGN PATENT DOCUMENTS

TW        M258201        3/2005

OTHER PUBLICATIONS

English translation of abstract of TW M258201.
Taiwan Office Action mailed Aug. 10, 2012.
English translation of pertinent parts of Taiwan Office Action mailed Aug. 10, 2012.

* cited by examiner

*Primary Examiner* — Sunil K Singh
(74) *Attorney, Agent, or Firm* — McClure, Qualey & Rodack, LLP

(57) ABSTRACT

An artificial root for dental implantation comprises a neck portion, an end portion opposite the neck portion, a body portion and a multiplex thread structure which is formed on the body portion. The multiplex thread structure comprises a first thread and a second thread in which the first thread forms a root portion with a specific first width for the second thread, which has a crest portion of a specific second width, to be accommodated into the root portion. The multiplex thread structure is partially configured in such a way that the second width of the crest portion is simultaneously increased when the first width of the root portion is gradually increased.

6 Claims, 5 Drawing Sheets

ARTIFICIAL ROOT FOR DENTAL IMPLANTATION AND METHOD FOR MANUFACTURING THE SAME

CROSS-REFERENCES TO RELATED APPLICATIONS

Not applicable.

BACKGROUND OF THE INVENTION

1. Field of the Invention

The present invention provides an artificial root for dental implantation and a method for manufacturing the artificial root. In particular, the present invention provides an artificial root for dental implantation with parametrically varied threads and a method for manufacturing the artificial root.

2. Descriptions of the Related Art

There are two stages in the growth of human teeth. Specifically, the permanent teeth, which are firmer and more solid, will come out after the baby teeth been extracted. Unlike baby teeth, permanent teeth cannot be reproduced, and can only be repaired or completely removed if the tooth is seriously damaged. The damage or absence of the tooth not only causes defects in the appearance, but may also cause dislocation of the adjacent teeth, resulting in chewing and speaking difficulty. To restore the appearance and improve chewing and speaking, patients often visit the dentist to repair or extract the damaged tooth.

In the dental technology field, tooth caps and bridges are conventionally used to repair teeth or consolidate intertooth structures. The method utilizes the two adjacent teeth as pillars for supporting the crown and the bridge. However, this method may negatively affect the healthy adjacent teeth. For example, two adjacent teeth have to be cut, ground or shaved down to accommodate the tooth caps and bridges that will be disposed therebetween. As a result, the two otherwise healthy teeth are compromised during this process.

With the advancement of science and technologies, dental implantation technology has also been developed. Specifically, an artificial tooth root is implanted directly into an alveolar bone to completely replace the damaged tooth. Since the artificial dental implantation requires no additional devices and support from adjacent teeth, it is less likely to damage adjacent natural teeth and may prevent atrophy of the alveolar bone and the gum, thus maintaining the long-term health and functions of the oral cavity.

In 1950, a Sweden Professor Per-Ingvar Branemark discovered that titanium has great biocompatibility with the human body. That is, there is a lower chance for the human body to reject the titanium, allowing the bone tissue to grow on and integrate on the surface of titanium. Therefore, P-I Branemark proposed the concept of osseointegration and applied the concept into the dental field, thereby making a breakthrough in denture technology.

Due to the progression of science, the denture technology has also becoming more advanced and reliable. The denture process nowadays is carried out by implanting an artificial root with a titanium surface into the alveolar bone where the tooth is extracted. When the artificial root has been implanted, one of conventional treatments is to temporarily stitch up the opening of the gingiva. It may take about three to six months for the osseointegration of the alveolar bone and the artificial root. After the osseointegration is complete and the newly grown bone tissue is tightly integrated with the titanium, the gingivae will be reopened and an abutment will be fixed onto the artificial root. A crown will be further installed on the abutment as the last step in replacing the damaged tooth.

Because the artificial denture does not require the bridge to connect to adjacent teeth as support, the adjacent teeth do not have to be cut, ground and damaged. In addition, there is no atrophy in the alveolar bone and gingivae. To maintain oral health and proper function of the teeth, restoring lost portions of teeth with the implantation of artificial dentures has become increasingly popular.

However, there are still risks in the denture process. When the bone tissue is growing and integrating onto the surface of the artificial root, the micro-motion therebetween should be prevented. The micro-motion may cause the bone tissue to loosen from the surface of the artificial root, causing a failure in osseointegration.

To increase the securing effect and prevent the osseointegration failure, conventional artificial denture roots are disclosed with threads formed on the surface thereof, so that the denture process is carried out by threading the artificial root into the alveolar bone. By this configuration, the artificial root and the alveolar bone can be tightly engaged with each other with the mechanical force provided by the thread in the early stage of the osseointegration, thereby preventing the micro-motion and facilitating the integration of the bone tissue on the surface of the artificial root. Thus, after the denture process is completed, the integration between the alveolar bone and the artificial root relies not only on the surface bonding force therebetween but also relies on the engaged mechanical force to achieve better integration. The artificial root with the thread formed thereon is therefore able to sustain chewing force.

The thread profile of an artificial root is very different from the thread that is commonly seen in other technical fields. A common thread will experience a less tightening force after the initial groove has been formed by the thread during the threading process. However, to better secure the artificial root implantation in the alveolar bone, the thread profile thereof is often specially designed so that the tightening force is increased during the threading process.

The conventional thread structures focus on increasing the lateral force to provide more security. An example of increasing lateral force is to increase the height of the thread that engages with the alveolar bone so that it is deeper during the artificial root implantation. However, the lateral force does not provide enough resistance from micro-motion. In addition, the variation of thread may cause excessive heat in the bone tissue due to a greater tightening force and greater fiction between the alveolar bone and the surface of the artificial root during the threading process. When the bone tissue is heated up over a temperature of 47 Celsius degrees, the cells of the bone tissue will be permanently damaged and the denture implantation will fail. On the other hand, if the artificial root is threaded with a lower speed into the alveolar bone to reduce the generated heat, the surgery time will be prolonged and cause the patient to be uncomfortable for a longer period of time.

Furthermore, if the conventional artificial root is designed in a thread with varied thickness, a plurality of cutting tools should be utilized during manufacture. The varied thread manufactured by various cutting tools is not able to be smooth.

In view of this, it is highly desirable in the art to provide an artificial root with a thread profile in a way that facilitates the implantation and provides more security and faster patient recovery after the surgery. In addition, a novel manufacturing method for making the artificial root is desired.

SUMMARY OF THE INVENTION

The objective of this invention is to provide an artificial root for dental implantation. The artificial root comprises a neck portion, an end portion opposite the neck portion, a body portion and a multiplex thread structure. The body portion is defined between the neck portion and the end portion. The multiplex thread structure is formed on the surface of the body portion and comprises a first and second thread. The first thread forms a root portion with a first width for the second thread to be accommodated therein. The second thread has a crest portion with a second width. The multiplex thread structure is partially configured in such a way so that the second width of the crest portion is simultaneously increased when the first width of the root portion is gradually increased.

Another objective of this invention is to provide a method for manufacturing the artificial root for dental implantation. The artificial root comprising a neck portion, an end portion opposite the neck portion and a body portion defined between the neck portion and the end portion. The method comprises the following steps: forming a first helical groove on the body portion; and forming a second helical groove along and partially overlapping with the first helical groove on the body portion; wherein either the first helical groove and/or the second helical groove is parametrically varied in pitch.

Thus, the present invention discloses the artificial root with a multiple thread profile that provides better security. The thread interferes and compresses the alveolar bone to increase the axial force by parametrically varying the threads but to merely increase the lateral force during osseointegration. The artificial root of the present invention also has a configuration that facilitates the implantation and increases the contact area with the alveolar bone. The present invention further provides a simpler manufacturing method for making the artificial root with a smooth parametrically varied thread profile without frequently changing the cutting tools.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
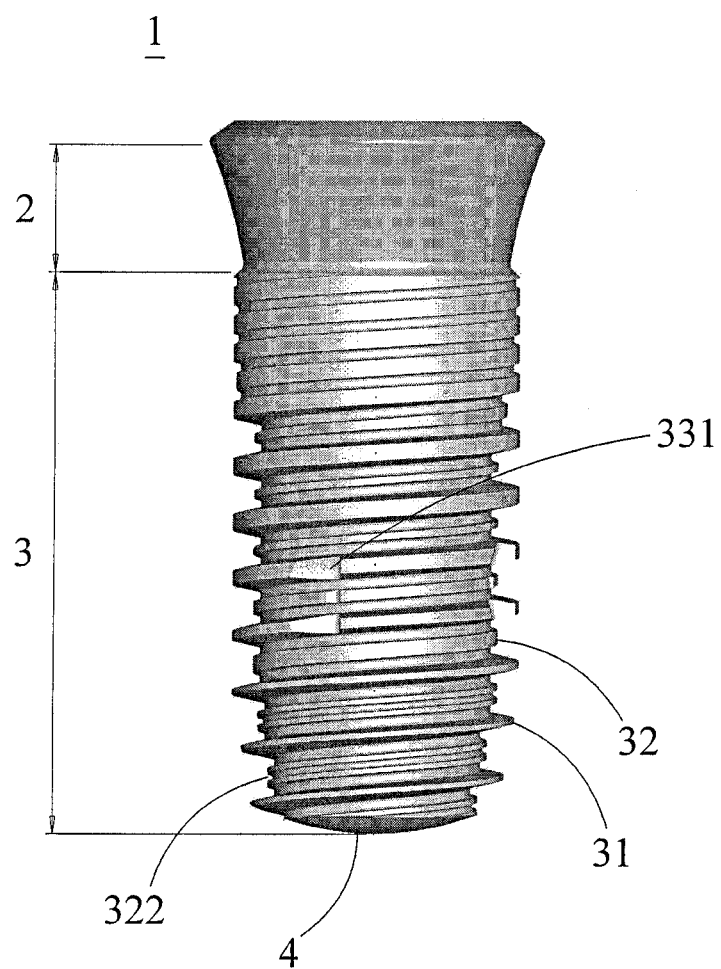
FIG. 1 is a schematic view of the artificial root according to an embodiment of this invention.
Figure 2:
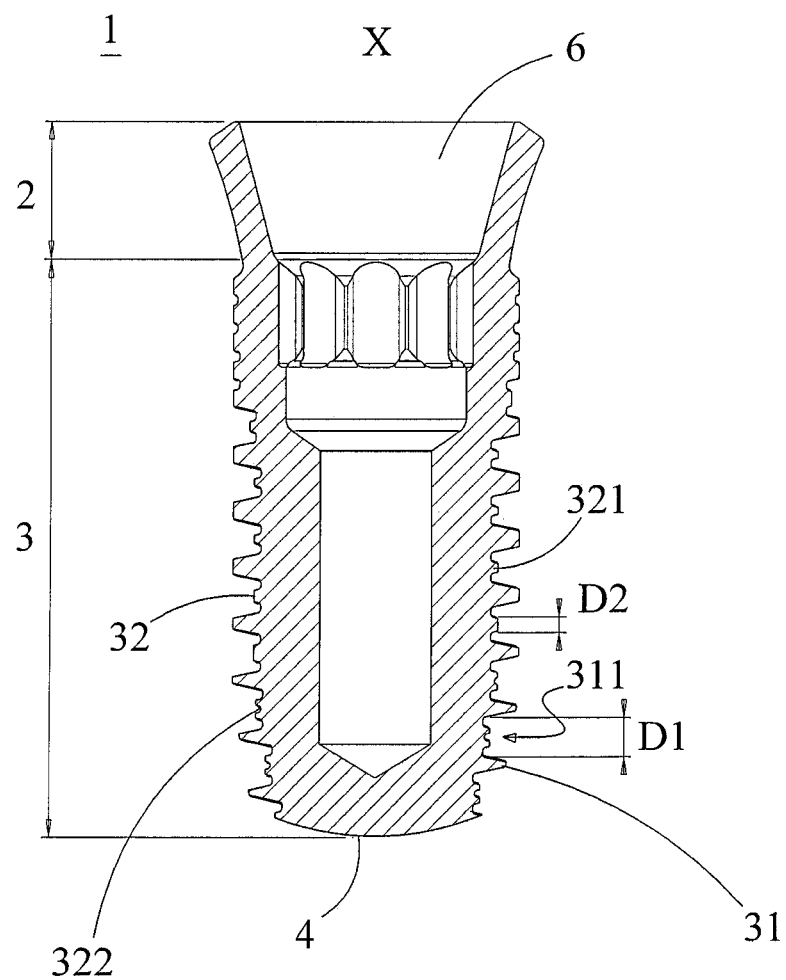
FIG. 2 is a cross-sectional view of the artificial root according to the embodiment of this invention shown in FIG. 1.

FIG. 1 and FIG. 2 illustrate an artificial root for dental implantation in the embodiment of this invention. The artificial root 1 comprises a neck potion 2, a body portion 3 and an end portion 4. The neck potion 2 is at one end of the artificial root 1, while the end portion 4 is at the other end opposite the neck portion 2. The body portion 3 is defined between the neck portion 2 and the end portion 4. Additionally, a connecting structure 6, for example, a screw hole, is formed from the neck portion 2 into the body portion 3. The connecting structure 6 is adapted to be connected with an abutment (not shown) when the gum is reopened once the osseointegration stage is completed. The present invention is unique in that a multiplex thread structure is formed on the surface of the body portion 3. In this embodiment, the multiplex thread structure is a twin helical thread structure comprising a first thread 31 and a second thread 32. It is noted that the twin helical thread structure in this embodiment is utilized to disclose the invention, but is not limited thereto.

The first thread 31 is the main thread that provides a larger tightening force especially during the previous osseointegration stage. The second thread 32 is capable of contributing to the tightening force and increasing the contact surface area between the artificial root and the alveolar bone. The increasing surface area can facilitate osseointegration.

The multiplex thread structure has a the first thread 31 that is formed with a root portion 311 of a specific first width D1 and a second thread 32 that is formed with a crest portion 321 with a specific second width D2 in such a way that the second thread 32 is adapted to be accommodated within the root portion 311 of the first thread 31. With such a configuration, the first thread 31 and the second thread 32 together form a twin helical threads structure.

To provide a sufficient securing force without excessively increasing the lateral pressure exerted onto the alveolar bone, which may cause too much damage, the first width D1 of the root portion 311 of the first thread 31 is partially configured to be gradually increased towards the end portion 4. That is to say, the first thread 31 has a thickness partially increased from the end portion 4 towards the neck portion 2. By threading the artificial root into the alveolar bone, the bone tissue fitted into the root portion 311 of the first thread 31 will experience a wider first width D1 initially and a decreasing first width D1 during the threading process. Because the first thread 31 has an increasing thickness from the end portion 4 towards the neck portion 2, this will provide a compressing force on the bone tissue in the axial direction X of the artificial root and thus, provides more security without exerting excessive force in the lateral direction.

Furthermore, the thread structure is partially configured in such a way so that the second width D2 of the crest portion 321 of the second thread 32 is simultaneously increased when the first width D1 of the root portion 311 of the first thread 31 is gradually increased. More specifically, in this embodiment, the first thread 31 partially gets thicker towards the neck portion 2, i.e. the root portion 311 is getting smaller. Simultaneously, the second thread 32 is getting thinner. Thus, the multiplex thread structure can be manufactured more simply. Additionally, the crest portion 321 of the second thread 32 is partially formed with a groove 322 where the second thread 32 is adjacent to the end portion. This will increase the contact area between the body portion 3 and the alveolar bone and thus, enhance osseointegration.

Figure 3:
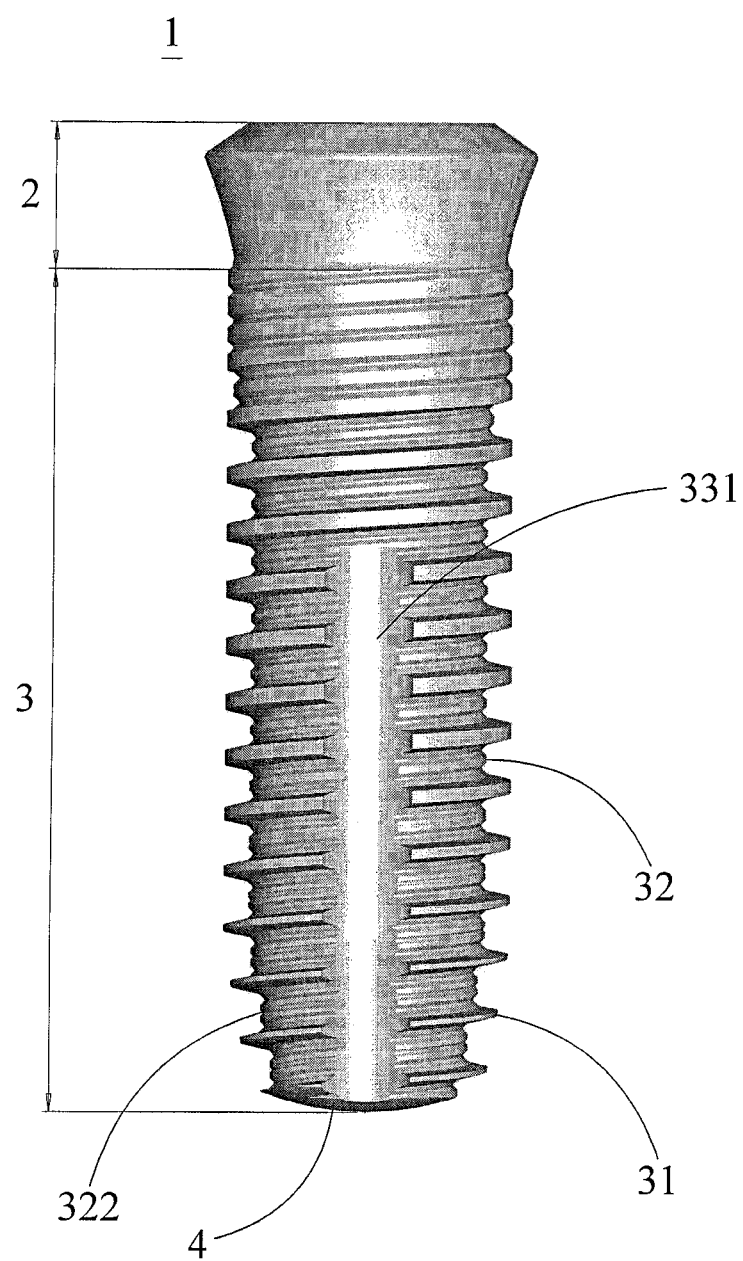
FIG. 3 is a schematic view illustrating another embodiment of the artificial root of this invention.

The artificial root 1 of the present invention has a tapping groove 331 that is formed on the body portion 3. As shown in FIG. 1 and FIG. 2, the tapping groove 331 is formed on the middle portion of the body portion 3. In another embodiment, the tapping groove 331 extends along the axial direction X on the body portion 3 towards the end portion 4, as shown in FIG. 3. Also, the body portion 3 of the artificial root 1 of the present invention is tapered towards the end portion 4. Thus, when the artificial root 1 is implanted and threaded into the alveolar bone, it is more precise and stable in the direction and position of the initial stage. The tapping groove 331 helically grooves the alveolar bone after the front end is located in the alveolar bone to facilitate the engagement of the following threads.

At the outer portion of the alveolar bone, i.e. the cortical bone, which is corresponding to the body portion 3 adjacent to the neck portion 2 after the artificial root 1 is implanted, the bone density is denser and is adapted to bear greater force without been deformed and damaged. Therefore, the second thread 32 of this invention has an increasing thickness and diameter when the second thread 32 is towards the neck portion 2. The first thread 31 and the second thread 32 are substantially identical where they are adjacent to the neck portion 2 to provide a stronger securing force for the artificial root 1.

Figure 4:
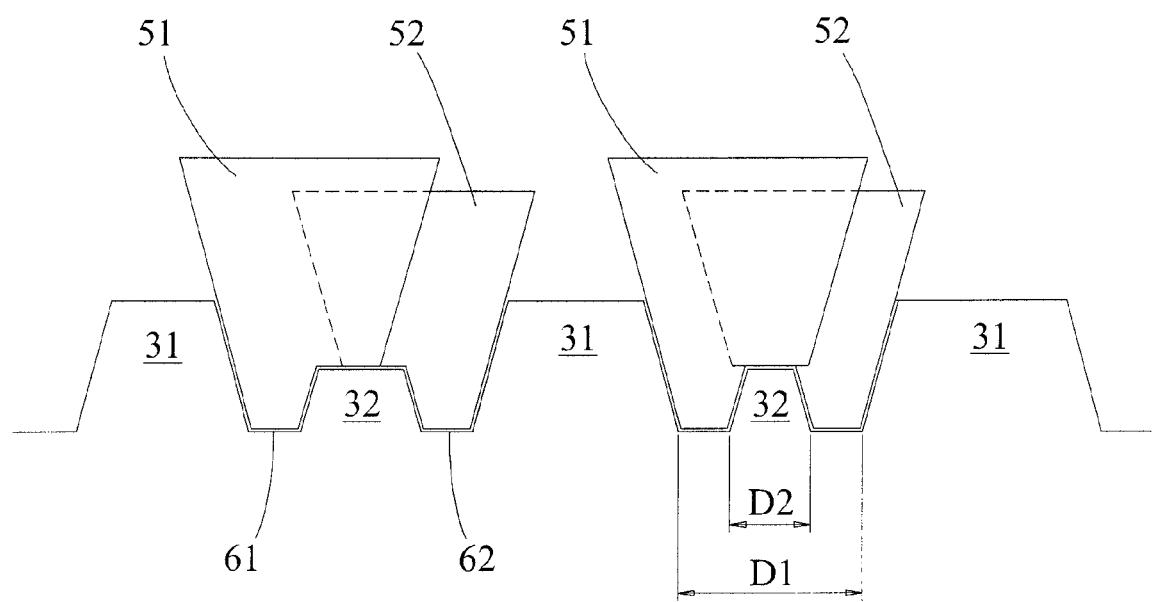
FIG. 4 is a partially enlarged view illustrating a method of manufacturing the thread profile of the artificial root of the present invention.

This invention further provides a method for manufacturing the artificial root 1 described above. In reference to FIG. 4, two cutting tools are involved in this embodiment. More specifically, the first cutting tool 51 is utilized to form, e.g. to lathe, the first helical groove 61 on the body portion 3. Then, the second cutting tool 52 is utilized to form, e.g. to lathe, the second helical groove 62 on the body portion 3, along the first helical groove 61. In actuality, the first helical groove 61 and the second helical groove 62 are partially overlapping. The first helical groove 61 and the second helical groove 62 are adapted to define a first thread 31 and a second thread 32 on the body portion 3. More specifically, the first helical groove 61 has a first cross-section, while the second helical groove 62 has a second cross-section. The first helical groove 61 and the second helical groove 62 are adapted to define the root portion 311 of the first thread 31 and a crest portion 321 of the second thread 32. The method disclosed in the present invention is unique in that either the first helical groove 61 and/or the second helical groove 62 is parametrically varied in pitch; that is, either the first cutting tool 51 or the second cutting tool 52 is parametrically and relatively moved when lathing the body portion 3. For example, the first cutting tool 51 and the second cutting tool 52 can come towards each other to form the first width D1 of the root portion 311 of the first thread 31 gradually decreased as it goes towards the neck portion 2. Simultaneously, the size of the second width D2 of the crest portion 321 of the second thread 32 is simultaneously decreased. In reference to FIGS. 1 and 2 again, the root portion 311 has a first width D1, while the crest portion 321 has a second width D2 in which the second width D2 is simultaneously decreased when the first width D1 is gradually decreased and vice versa.

Figure 5A:
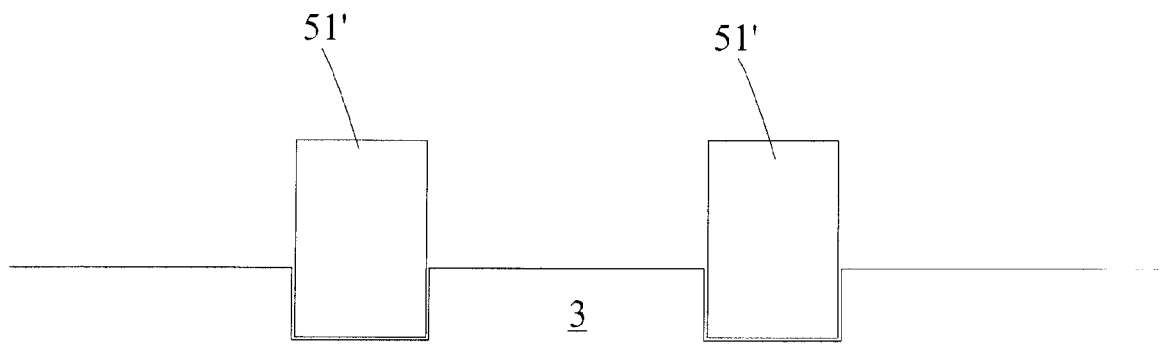
FIGS. 5A and 5B are partially enlarged views illustrating another method of manufacturing the thread profile of the artificial root of the present invention.
Figure 5B:
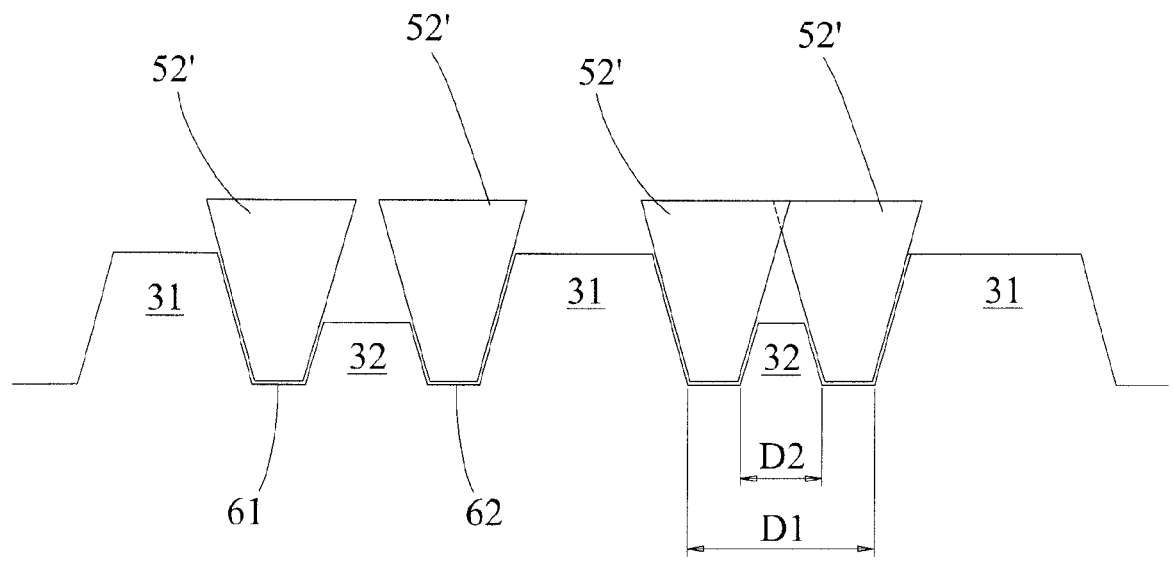

As shown in FIG. 5A and FIG. 5B, the present invention provides another method for manufacturing the artificial root 1. First, FIG. 5A illustrates the first cutting tool 51' which is utilized to lathe a helical groove on body portion 3 with respect to the crest portion 321 of the second thread 32. Then, as shown in FIG. 5B, the second cutting tool 52' is utilized to lathe the body portion 3 twice with parametrically varied pitch, to form the first helical groove 61 and the second helical groove 62. It is noted that the manufacturing procedure of using the first cutting tool 51' and the second cutting tool 52' is not limited. For example, the second cutting tool 52' could be utilized first to form the helical grooves 61 and 62. Then, the first cutting tool 51' is utilized to define the crest portion 321 of the second thread 32. Similar to the above-mentioned embodiment, the first helical groove 61 and the second helical groove 62 are adapted to define the first thread 31 and the second thread 32 on the body portion 3 in a configuration that the second width D2 of the crest portion 321 of the second thread 32 is simultaneously decreased when the first width D1 of the root portion 311 of the first thread 31 is gradually decreased and vice versa. Certainly, using the second cutting tool 52' twice to form the first helical groove 61 and the second helical groove 62 is not limited. A person skilled in the art may use two different cutting tools to form the first helical groove 61 and the second helical groove 62, respectively.

It is noted that the double helical thread structure is just exemplified for illustration and not for limitation. The concept of using two cutting tools for manufacturing the double helical threads structure may be utilized to manufacture a single helical thread structure or even a triple helical threads structure, which can be achieved by using different profile designs on the cutting tools.

Thus, the artificial root of the present invention is manufactured by the cutting tools which are parametrically shifted to form the multiple thread profile that provides better axial security during osseointegration. It is a simpler manufacturing method for making the artificial root with a smooth varied thread profile without changing the cutting tools. Furthermore, the tapping groove formed on the body portion additionally enhances the stability in the initial implantation stage.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An artificial root for dental implantation, comprising:
   a neck portion;
   an end portion for implanting, which is opposite the neck portion;
   a body portion defined between the neck portion and the end portion; and
   a multiplex thread structure formed on a surface of the body portion from the end portion toward an end approaching to the neck portion, the multiplex thread structure at least comprising a first thread and a second thread;
   wherein the first thread forms a root portion with a first width for the second thread which has a crest portion with a second width being accommodated therein, and the multiplex thread structure is configured in such a way that the second width of the crest portion is simultaneously increased when the first width of the root portion gradually increases along the surface of the body portion, the first width of the root portion of the first thread gradually increases towards the end portion, and the first thread has a thickness increasing along the surface of the body portion from the end portion towards the neck portion.

2. The artificial root as claimed in claim 1, wherein the multiplex thread structure is a twin helical thread structure.

3. The artificial root as claimed in claim 1, wherein the crest portion of the second thread is partially formed with a groove where the second thread is adjacent to the end portion.

4. The artificial root as claimed in claim 2, wherein the body portion is tapered towards the end portion.

5. The artificial root as claimed in claim 2, further comprising a tapping groove formed on the body portion.

6. The artificial root as claimed in claim 2, wherein the first thread and the second thread are substantially identical where they are adjacent to the neck portion.

* * * * *